US006458981B1

(12) United States Patent
Ashmead et al.

(10) Patent No.: US 6,458,981 B1
(45) Date of Patent: Oct. 1, 2002

(54) COMPOSITION AND METHOD FOR PREPARING AMINO ACID CHELATE HYDROXIDES FREE OF INTERFERING IONS

(75) Inventors: Stephen D. Ashmead, Clinton; David C. Wheelwright, Layton; Clayton Ericson, Morgan; Mark Pedersen, Kaysville, all of UT (US)

(73) Assignee: Albion International, Inc., Clearfield, UT (US)

( * ) Notice: Subject to any disclaimer, the term of this patent is extended or adjusted under 35 U.S.C. 154(b) by 0 days.

(21) Appl. No.: 09/686,046

(22) Filed: Oct. 11, 2000

(51) Int. Cl.⁷ .............................. C07F 3/00; C07F 11/00; C07F 13/00; C07F 15/00
(52) U.S. Cl. ........................ 556/50; 556/63; 556/116; 556/134; 556/148
(58) Field of Search ............................ 556/50, 63, 116, 556/134, 148

(56) References Cited

U.S. PATENT DOCUMENTS

| | | |
|---|---|---|
| 2,877,253 | 3/1959 | Rummel ..................... 260/439 |
| 2,957,806 | 10/1960 | Rummel ..................... 167/68 |
| 2,960,406 | 11/1960 | Cardon ........................... 99/2 |
| 3,396,104 | 8/1968 | Miller .......................... 210/54 |
| 3,463,858 | 8/1969 | Anderson .................... 424/289 |
| 3,775,132 | 11/1973 | Richards, Jr. ................ 426/364 |
| 4,020,158 | 4/1977 | Ashmead et al. ............ 424/177 |
| 4,103,003 | 7/1978 | Ashmead ..................... 424/177 |
| 4,167,564 | 9/1979 | Jensen ......................... 424/177 |
| 4,172,072 | 10/1979 | Ashmead ..................... 260/115 |
| 4,216,143 | 8/1980 | Ashmead ..................... 260/113 |
| 4,216,144 | 8/1980 | Ashmead ..................... 260/115 |
| 4,599,152 | 7/1986 | Ashmead ...................... 204/72 |
| 4,725,427 | 2/1988 | Ashmead et al. .............. 424/44 |
| 4,774,089 | 9/1988 | Ashmead ..................... 424/157 |
| 4,830,716 | 5/1989 | Ashmead ...................... 204/72 |
| 4,863,898 | 9/1989 | Ashmead ....................... 514/6 |

*Primary Examiner*—Porfirio Nazario-Gonzalez
(74) *Attorney, Agent, or Firm*—Thorpe, North & Western, LLP

(57) ABSTRACT

The present invention relates to compositions and methods of preparing amino acid chelates that are essentially free of interfering ions. The composition is prepared by reacting in an aqueous solution, a calcium oxide and/or hydroxide, an amino acid, and a soluble metal sulfate salt at a ratio sufficient to allow substantially all of the ions present in solution to react forming a positively charged metal amino acid chelate having a hydroxide counter-ion, and calcium sulfate, and wherein the metal amino acid chelate has a ligand to metal molar ratio from 1:1 to 2:1.

25 Claims, No Drawings

COMPOSITION AND METHOD FOR PREPARING AMINO ACID CHELATE HYDROXIDES FREE OF INTERFERING IONS

FIELD OF THE INVENTION

The present invention relates to compositions and methods of preparing amino acid chelates that are essentially free of interfering ions with the proviso a hydroxide ion is not considered to be interfering. The composition is prepared by reacting in an aqueous environment a calcium oxide and/or hydroxide, an amino acid, and a soluble metal sulfate salt at a ratio sufficient to allow substantially all of the ions present in solution to react forming a charged metal amino acid chelate having a hydroxide counter-ion, an essentially inert calcium sulfate, and optionally, water. The metal amino acid chelates of the present invention have a ligand to metal molar ratio from about 1:1 to 2:1.

BACKGROUND OF THE INVENTION

Amino acid chelates are generally produced by the reaction between α-amino acids and metal ions having a valence of two or more to form a ring structure. In such a reaction, the positive electrical charge of the metal ion is neutralized by the electrons available through the carboxylate or free amino groups of the α-amino acid.

Traditionally, the term "chelate" has been loosely defined as a combination of a metallic ion bonded to one or more ligands forming heterocyclic ring structures. Under this definition, chelate formation through neutralization of the positive charges of the divalent metal ions may be through the formation of ionic, covalent, or coordinate covalent bonding. An alternative and more modern definition of the term "chelate" requires that the metal ion be bonded to the ligand solely by coordinate covalent bonds forming a heterocyclic ring. In either case, both definitions describe a metal ion and a ligand forming a heterocyclic ring.

A chelate is a definite structure resulting from precise requirement of synthesis. Proper conditions must be present for chelation to take place, including proper mole ratios of ligands to metal ions, pH, and solubility of reactants. For chelation to occur, all components are generally dissolved in solution and are either ionized or of appropriate electronic configuration in order for coordinate covalent bonding and/or ionic bonding between the ligand and the metal ion to occur.

Chelation can be confirmed and differentiated from mixtures of components by infrared spectra through comparison of the stretching of bonds or shifting of absorption caused by bond formation. As applied in the field of mineral nutrition, there are two allegedly "chelated" products which are commercially utilized. The first is referred to as a "metal proteinate." The American Association of Feed Control officials (AAFCO) has defined a "metal proteinate" as the product resulting from the chelation of a soluble salt with amino acids and/or partially hydrolyzed protein. Such products are referred to as the specific metal proteinate, e.g., copper proteinate, zinc proteinate, etc. Sometimes, metal proteinates are even referred to as amino acid chelates, though this characterization is not accurate. This is because by definition, a metal proteinate must contain partially hydrolyzed proteins which may or may not be mixed with amino acids.

The second product, referred to as an "amino acid chelate," when properly formed, is a stable product having one or more five-membered rings formed by a reaction between the carboxyl oxygen, and the α-amino group of an α-amino acid with the metal ion. Such a five-membered ring is defined by the metal atom, the carboxyl oxygen, the carbonyl carbon, the a-carbon and the α-amino nitrogen. The actual structure will depend upon the ligand to metal mole ratio and whether the carboxyl oxygen forms a coordinate covalent bond or an ionic bond with the metal ion. Generally, the ligand to metal molar ratio is at least 1:1 and is preferably 2:1 or 3:1. However, in certain instances, the ratio may be 4:1. Most typically, an amino acid chelate may be represented at a ligand to metal molar ratio of 2:1 according to Formula 1 as follows:

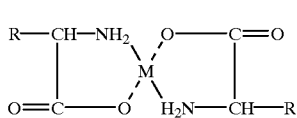

Formula 1

In the above formula, the dashed lines represent coordinate covalent bonds, covalent bonds, or ionic bonds. The solid lines between the α-amino group and the metal (M) are covalent or coordinate covalent bonds. Further, when R is H, the amino acid is glycine which is the simplest of the α-amino acids. However, R could be a radical forming any other of the other twenty or so naturally occurring amino acids derived from proteins. All of the amino acids have the same configuration for the positioning of the carboxyl oxygen and the α-amino nitrogen with respect to the metal ion. In other words, the chelate ring is defined by the same atoms in each instance, even though the R group may vary.

The American Association of Feed Control Officials (AAFCO) have also issued a definition for amino acid chelates. It is officially defined as the product resulting from the reaction of a metal ion from a soluble metal salt with amino acids having a mole ratio of one mole of metal to one to three (preferably two) moles of amino acids to form coordinate covalent bonds. The average weight of the hydrolyzed amino acids must be approximately 150 and the resulting molecular weight of the chelate must not exceed 800. The products are identified by the specific metal forming the chelate, e.g., iron amino acid chelate, copper amino acid chelate, etc.

The reason a metal atom can accept bonds over and above the oxidation state of the metal is due to the nature of chelation. For example, at the α-amino group of an amino acid, the nitrogen contributes both of the electrons used in the bonding. These electrons fill available spaces in the d-orbitals forming a coordinate covalent bond. Thus, a metal ion with a normal valency of +2 can be bonded by four bonds when fully chelated. In this state, the chelate is completely satisfied by the bonding electrons and the charge on the metal atom (as well as on the overall molecule) is zero. As stated previously, it is possible that the metal ion be bonded to the carboxyl oxygen by either coordinate covalent bonds or ionic bonds. However, the metal ion is typically bonded to the α-amino group by coordinate covalent bonds only.

Amino acid chelates can also be formed using small peptide ligands instead of single amino acids. These will usually be in the form of dipeptides, tripeptides, and sometimes tetrapeptides because larger ligands have molecular weights that are too great for direct cellular assimilation of the chelate formed. Generally, peptide ligands will be derived by the hydrolysis of protein. However, peptides prepared by conventional synthetic techniques or genetic engineering can also be used. When a ligand is a di- or tripeptide, a radical of the formula [C(O)CHRNH]$_e$ H will replace one of the hydrogens attached to the nitrogen atom in Formula 1. R, as defined in Formula 1, can be H, or the residue of any other naturally occurring amino acid and e can be an integer of 1, 2 or 3. When e is 1 the ligand will be a dipeptide, when e is 2 the ligand will be a tripeptide and so forth.

The structure, chemistry and bioavailability of amino acid chelates is well documented in the literature, e.g. Ashmead et al., Chelated Mineral Nutrition, (1982), Chas. C. Thomas Publishers, Springfield, Ill.; Ashmead et al., Intestinal Absorption of Metal Ions, (1985), Chas. C. Thomas Publishers, Springfield, Ill.; Ashmead et al., Foliar Feeding of Plants with Amino Acid Chelates, (1986), Noyes Publications, Park Ridge, N.J.; U.S. Pat. Nos. 4,020,158; 4,167,564; 4,216,143; 4,216,144; 4,599,152; 4,774,089; 4,830,716; 4,863,898; 4,725,427; and others, the entire teachings of which are incorporated by reference.

One advantage of amino acid chelates in the field of mineral nutrition is attributed to the fact that these chelates are readily absorbed in the absorptive mucosal cells or plant cells by means of active transport or other know mechanisms. In other words, the minerals are absorbed along with the amino acids as a single unit utilizing the amino acids as carrier molecules. Therefore, the problems associated with the competition of ions for active sites and the suppression of specific nutritive mineral elements by others are avoided. This is especially true for compounds such as iron sulfates that must be delivered in relatively large quantities in order for the body or plant to absorb an appropriate amount. This is significant because large quantities often cause nausea and other gastrointestinal discomforts in animals as well as create an undesirable taste. Additionally, in plants, large amounts of these compounds can act to burn leaves and cause other undesirable results.

In the past, amino acid chelates have generally been made by first dissolving a water soluble metal salt in water. An amino acid ligand is then reacted with the metal ion at a ratio of ligand to metal from 1:1 to 4:1, preferably 2:1. Often, the ligand is a hydrolysis product obtained by acid, base, base-acid, base-acid-base, or enzyme hydrolysis. In such cases, the by products from hydrolysis, such as anions including chlorides, sulfates, phosphates and nitrates, and cations including potassium and sodium, remain in the hydrolysate. Reaction products of metal salts with proteins or with acid and/or base hydrolyzed proteins are taught in U.S. Pat. Nos. 2,960,406; 3,396,104; 3,463,858; 3,775,132; 4,020,158; 4,103,003; and 4,172,072.

In fact, most water soluble salts used in making amino acid chelates have been either sulfates or chlorides. Using the sulfate ion as exemplary, the reaction has generally proceeded according to Formula 2 as follows:

Formula 2

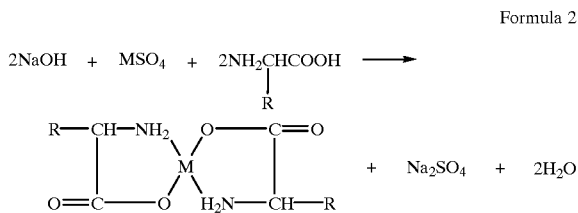

where M is a bivalent metal cation and R is a radical of a naturally occurring amino acid, dipeptide or polypeptide. It is apparent from the above formula that the sulfate anion is present in the reaction mixture in the form of sodium sulfate.

U.S. Pat. No. 2,877,253 teaches a product formed by the reaction of one mole of glycine with one mole of ferrous sulfate. That patent indicates that the sulfate anion becomes tied up in the reaction which allegedly forms a ferrous sulfate-glycine complex. Whether the sulfate actually participates in the reaction or is merely present as the salt of an alkali metal, it nevertheless is present in the reaction mixture. Thus, in many cases, the sulfate interferes with the total reaction and absorption of the chelate. Such products are difficult to purify. While sodium sulfate, per se, is water soluble, the reaction between a metal sulfate and an amino acid is never carried to 100% completion and the sulfate ion is always present. The same holds true for the presence of chloride ions when utilizing a metal chloride salt for amino acid chelate preparation.

Even if one were to attempt to wash out the excess sulfate or chloride ions with repeated washes, such an attempt would likely be counter productive inasmuch as glycine and other amino acid ligands are also soluble to a degree. Hence, depending upon pH, the unreacted ligands or weakly held ligands could also be removed along with the unwanted anions.

As mentioned, in order to manufacture amino acid chelates, it generally requires that the metal salt and the ligand both be dissolved in water. One problem with this is employing metal salts that are soluble but essentially free from anions that can interfere with the chelation process. This is the subject of U.S. Pat. Nos. 4,599,152 and 4,830, 716, both of which are incorporated by reference.

In the past, if certain soluble metal salts, such as sulfates, were used as a mineral source for chelation purposes, the resulting anions interfered with the chelation process. For example, the attraction between the lone pair of electrons on the amine group of an amino acid and a hydrogen ion is strong. This is why glycine is represented by the zwitterionic structure $^+H_3NCH_2COO^-$. This strong attraction for the hydrogen ion explains why amino acids are weak acids, e.g., glycine is not easily deprotonated. In water, only about 0.5% of the glycine typically disassociates and releases a hydrogen ion. Additionally, in the prior art, the introduction of mineral acid salts into solution, such as copper sulfate, resulted in the creation of copper ions which compete with the hydrogen ion for the lone pair of electrons on the NH$_2$ group. Unfortunately, the equilibrium favors the majority of the amino groups remaining protonated. Thus, in order to efficiently chelate metal ions from certain soluble salts, it becomes desirable to render the interfering ions inactive or use soluble metal salts with non-interfering ions, such as oxides or hydroxides.

SUMMARY OF THE INVENTION

The present invention comprises compositions and methods of manufacturing amino acid chelates free of interfering ions. These amino acid chelates are prepared by reacting calcium oxide or hydroxide, an amino acid, and a soluble metal sulfate salt in an aqueous environment at a ratio sufficient to allow substantially all of the potentially interfering ions present in solution to react. Thus, a positively charged metal amino acid chelate having a hydroxide counter ion present, an essentially insoluble calcium sulfate salt, and optionally, water are formed without the presence of interfering ions. As stated, for purposes of the present invention, a hydroxide anion is not considered to be interfering. The metal amino acid chelates produced will have a ligand to metal molar ratio from about 1:1 to 2:1, depending on the valency of the metal, e.g., Fe(II) forms 1:1 and Fe(III) forms 2:1.

DETAILED DESCRIPTION OF THE INVENTION

Before the present invention is disclosed and described, it is to be understood that this invention is not limited to the particular process steps and materials disclosed herein because such process steps and materials may vary somewhat. It is also to be understood that the terminology used herein is used for the purpose of describing particular embodiments only. The terms are not intended to be limiting because the scope of the present invention is intended to be limited only by the appended claims and equivalents thereof.

It must be noted that, as used in this specification and the appended claims, the singular forms "a," "an," and "the" include plural referents unless the content clearly dictates otherwise.

"Interfering ion" is meant to include any cation or anion which would hinder the formation of the amino acid chelate and which remains in the composition as a charged ion that has not reacted to form either the charged amino acid chelate having a hydroxide counter-ion or the calcium sulfate salt. For purposes of the present invention, a hydroxide anion which is preferably complexed to the positively charged amino acid chelate is not considered to be an interfering ion.

"Metal amino acid chelate" or "amino acid chelate" shall include metal ions bonded to ligands forming heterocyclic rings. The bonds may be coordinate covalent, covalent, and/or ionic at the carboxyl oxygen group. However, at the α-amino group, the bond is typically a coordinate covalent bond. Preferred amino acids include all of the naturally occurring amino acids. Additionally, for purposes of the present invention, "amino acid chelate" shall further include any charged amino acid chelate that is electrically balanced by a hydroxide counter ion. For example, a trivalent cation having a ligand to metal molar ratio of 2:1 may be represented by the formula $M(AA)_2{}^+OH^-$ where M is the trivalent metal and AA is an amino acid. Additionally, a divalent cation having a ligand to metal molar ratio of 1:1 may be represented by the formula $M(AA)^+OH^-$ where M is the divalent metal and AA is an amino acid. If the amino acid chelate as a whole is in solution, the hydroxide anion and the charged chelate may be in solution or complexed together. If the amino acid chelate has been dried, the hydroxide anion and the charged chelate will likely be complexed.

"Metal" is meant to cover all nutritionally relevant metals that are more soluble as sulfate salts than calcium sulfate. Though calcium is a metal, for purposes of the present disclosure, calcium is specifically excluded within this definition unless the context clearly dictates otherwise.

"Soluble metal sulfate" or "soluble metal sulfate salt" include all divalent or trivalent metals that are more soluble than calcium sulfate when in the form of a sulfate salt. Preferred soluble metal sulfate salts are comprised of at least one nutritionally relevant metal.

"Nutritionally relevant metals" include metals that are known to be needed by living organisms, particularly plants and mammals, including humans. Metals such as copper (Cu), zinc (Zn), iron (Fe), cobalt (Co), magnesium (Mg), manganese (Mn), and/or chromium (Cr), among others, are exemplary of nutritionally relevant metals.

Essentially, the present invention includes compositions and methods of manufacturing amino acid chelates free of interfering ions. These chelates are prepared by reacting 1) a calcium oxide or hydroxide, 2) an amino acid, and 3) a soluble metal sulfate salt in an aqueous environment at a ratio sufficient to allow substantially all of the ions present in solution to react forming a positively charged metal amino acid chelate having a hydroxide counter-ion, a calcium sulfate salt, and optionally, water. Further, the metal amino acid chelates of the present invention will have a ligand to metal molar ratio from about 1:1 to 2:1.

The compositions and methods disclosed herein are similar to those described in the patent application filed of even date herewith entitled "A COMPOSITION AND METHOD FOR PREPARING ELECTRICALLY NEUTRAL AMINO ACID CHELATES FREE OF INTERFERING IONS," which is incorporated herein by reference (hereinafter referred to under 09/686,684 Oct. 11, 2000). However, a major difference between the present invention and that disclosed in T8148 is that the present invention discloses compositions and methods of preparing amino acid chelates having a ligand to metal molar ratio from about 1:1 to 2:1 that are charged and typically have a hydroxide counter-ion complexed thereto. In T8148, the amino acid chelates themselves are electrically neutral (not charged) and have a ligand to metal molar ratio from about 2:1 to 3:1.

The amino acid to be used in the present invention is preferably one or more of the naturally occurring amino acid selected from the group consisting of alanine, arginine, asparagine, aspartic acid, cysteine, cystine, glutamine, glutamic acid, glycine, histidine, hydroxyproline, isoleucine, leucine, lysine, methionine, ornithine, phenylalanine, proline, serine, threonine, tryptophan, tyrosine, valine, and combinations thereof. However, dipeptides, tripeptides, and tetrapeptides formed by any combination of the naturally occurring amino acids may also be used. The metal should be more soluble as a sulfate salt than calcium sulfate. Exemplary metals include those selected from the group consisting of Cu, Zn, Fe, Cr, Co, Mg, Mn, and combinations thereof. Therefore, the metal reactant is preferably provided as a sulfate salt selected from the group consisting of copper sulfate ($CuSO_4$), zinc sulfate ($ZnSO_4$), ferrous sulfate ($FeSO_4$), manganese sulfate ($MnSO_4$), cobalt sulfate ($CoSO_4$), magnesium sulfate ($MgSO_4$), ferric sulfate [$Fe_2(SO_4)_3$], chromic sulfate [$Cr_2(SO_4)_3$], and combinations thereof.

While not wanting to be bound by any theory, a possible mechanism of the process may be broken down into two steps. Step A involves the reaction of one or more amino acids with a calcium oxide or hydroxide in an aqueous environment forming a calcium amino acid chelate or complex product. Step B involves the reaction of one or more soluble metal sulfate salts with the calcium amino acid chelate or complex product formed in Step A. The calcium is displaced by the metal forming a charged metal amino acid chelate having a ligand to metal molar ratio from 1:1 to 2:1. Further, the calcium reacts with the sulfate anion to form an inert and highly insoluble calcium sulfate precipitate. By-products include the presence of a hydroxide counter-ion which is preferably complexed to the metal amino acid chelate balancing the charge of the positively charged chelate, and optionally, water.

The reactions used to prepare amino acid chelates essentially free of interfering ions and having a ligand to metal molar ratio from about 1:1 to 2:1 are shown below. Formulas 3a and 3b illustrate the production of an amino acid chelate having a 1:1 ligand to metal molar ratio:

Formula 3a

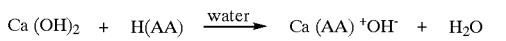
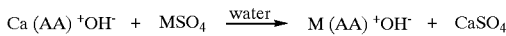

Formula 3b

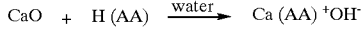
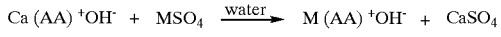

In Formulas 3a, 3b above and Formulas 4a and 4b below, (H)AA is an amino acid selected from the group consisting of naturally occurring amino acids and combinations thereof. H, when disassociated from AA, is a hydrogen ion donor from the carboxyl group present on the amino acid. M is a nutritionally relevant metal having a valency of +2 (excluding calcium) such as Cu, Zn, Fe, Co, Mg, and/or Mn.

To illustrate this mechanism further, consider the reactants copper sulfate, calcium oxide, and glycine. First, one mole of calcium oxide is reacted with one mole of glycine. After allowing the calcium and glycine to react, copper sulfate is added. The log of the equilibrium constant at zero ionic strength for the reaction $Ca^{2+}+(Gly)^- \longleftrightarrow Ca(Gly)^+$, where $(Gly)^-$ represents a glycine anion, is 1.39. By comparison, for the same reaction with copper rather than calcium, the log of the equilibrium constant is 8.56. Thus, these values demonstrate that copper has stronger affinity for the glycine ligand than does the calcium.

It is important to note that the added reactants, i.e., CaO or $Ca(OH)_2$, H(AA), and $MSO_4$, may be added in any order. For example, all three reactants may be added simultaneously or the amino acid and the soluble metal sulfate salt may be added before the calcium oxide or hydroxide. However, the above equation must be balanced to account for all of the potential interfering ions so that the final product (which includes $M(AA)^+OH^-+CaSO_4$) is free of interfering ions. Therefore, notwithstanding Formula 3a and 3b which illustrates the above mechanism, the general formula of the present invention when a 1:1 ligand to metal molar ratio is desired may be represented by Formulas 4a and 4b below:

Formula 4a

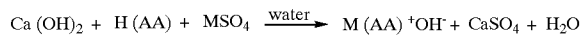

Formula 4b

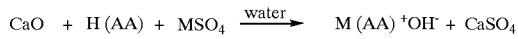

For purposes of the present invention, multiple soluble metal sulfate salts, amino acids, etc., may also be used. However, metals with proper oxidation states or valency should be used, e.g., Cu, Zn, Fe(II), Co, Mg, and/or Mn when producing amino acid chelates having a ligand to metal molar ratio of about 1:1.

General Formula 4 above may be modified to prepare amino acid chelates having a ligand to metal molar ratio of about 2:1 using nutritionally relevant metals having a valency of +3, e.g., Fe(III), Cr, etc. The general formula of the present invention when a 2:1 ligand to metal molar ratio is desired may be represented by Formulas 5a and 5b below:

Formula 5a

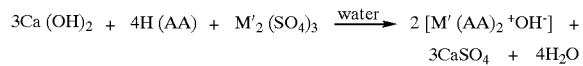

Formula 5b

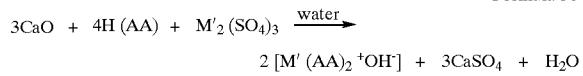

In Formulas 5a and 5b, H(AA) is an amino acid selected from the group consisting of naturally occurring amino acids and combinations thereof; H, when disassociated from AA, is a hydrogen ion donor from the carboxyl group present on the amino acid. M' is a nutritionally relevant metal having a valence of +3 such as Fe(III) and/or Cr.

It is important to note that though the compositions and methods of the present invention provide amino acid chelates free of interfering ions, calcium sulfate is always a byproduct. Therefore, the calcium sulfate may be substantially separated out of the compound by methods commonly known in the art. Alternatively, the calcium sulfate may remain in the compound as a stabilizer or for other purposes as described herein.

The present invention also encompasses drying of the chelate solution when appropriate to provide a powder form for some uses, e.g., human, animal, and plant nutrition. However, with some applications, it may be desired that the chelate remain in solution, e.g., foliar use. If drying the chelate to form a particulate, any conventional drying technique as is known in the art may be used. For example, if spray drying, bulk density of the powder produced in a spray dryer is affected by the mesh size of the nozzles in the dryer, the pump pressure, and the percent of total solids in the solution to be dried. In general, the higher the total solids, the greater the bulk density of the resulting powder. A greater bulk density also reduces the electrostatic properties of the spray dried powder. For example, the presence of the calcium sulfate (terra alba) suspended in the metal amino acid chelate solution by continual agitation will increase the total solids to be dried, thus, increasing the ultimate bulk density of the dried chelate.

The increased bulk density of the dried product can have at least three distinct advantages. First, the dried product is less hygroscopic due to the increased density and due to the fact that calcium sulfate salt is less hygroscopic than the amino acid chelate, which through the drying process have waters of hydration removed. Second, a more dense particle is less electrostatic. This potentially reduces the cleanup time in a mixer when the chelate is blended with other food or pharmaceutical substances and enhances mixing characteristics when powdered chelates are blended with these other substances. Third, when the amino acid chelate is mixed with calcium sulfate, the presence of calcium sulfate stabilizes the amino acid chelate in an acidic environment.

EXAMPLES

The following examples illustrate methods of preparing amino acid chelates that are essentially free of interfering ions. The following examples should not be considered as limitations of the present invention, but should merely teach how to make the best known amino acid chelates based upon current experimental data.

Each of the composition examples described herein provide an amount of chelate product produced in solution. However, often, the step of drying, i.e., removing moisture, from a chelate solution may be preferred. Prior to drying, calcium sulfate (terra alba) may be removed by separation techniques known by those skilled in the art if desired. Additionally, in every example, a hydroxide counter-ion is present for each amino acid chelate molecule formed.

Example 1

Preparation of Copper Glycine Amino Acid Chelate

Into about 1500 grams of water was dissolved 150.14 grams of glycine. Next, 114.51 grams of calcium oxide, which was 70% calcium by weight, was added. The solution was continually stirred until all of the calcium oxide was dissolved. This took about 15 minutes. No heat was applied for this particular reaction, though heat could optionally be used. The resulting reaction formed a calcium glycinate chelate or complex.

Next, 508.2 grams of copper sulfate pentahydrate containing 25% Cu by weight was added to the calcium chelate solution. Again, the solution was constantly stirred while the copper sulfate was dissolved. As the copper sulfate went into solution, a white precipitate of calcium sulfate formed. About 277 grams of a copper glycine amino acid chelate having a ligand to metal molar ratio of about 1:1 was produced.

Example 2

Preparation of Copper Alanine Amino Acid Chelate

A reaction mixture was prepared comprising 33.96 grams of calcium oxide, 108.09 grams of alanine, and 700 grams of water. The mixture was stirred for 15 minutes. Next, 301.83 grams of copper sulfate pentahydrate was added to the reaction mixture. As the solution was further stirred, a white precipitate of calcium sulfate formed. Once the reaction was complete, 205.15 grams of a copper alanine amino acid chelate having a ligand to metal molar ratio of about 1:1 remained in solution.

Example 3

Preparation of Iron Serine Amino Acid Chelate

A solution was prepared containing 58.23 grams of calcium oxide, 218.18 grams of serine, and 700 grams of water. The reaction mixture was stirred for about 15 minutes while the reaction advanced. Next, 261.89 grams of ferrous sulfate pentahydrate was added to the reaction mixture and stirred for about 15 minutes. In addition to the calcium sulfate precipitate (terra alba) produced, 367.35 grams of an iron serine amino acid chelate having a ligand to metal molar ratio of about 1:1 was produced.

Example 4

Preparation of Copper Lysine Amino Acid Chelate

A reaction mixture comprised of 5.58 grams of calcium oxide, 32.66 grams of lysine monohydrate, and 700 grams of water was prepared and allowed to react while stirring for 30 minutes. To the liquid reaction mixture, 49.94 grams of copper sulfate pentahydrate was added and stirred until the reaction appeared complete. A white precipitate of calcium sulfate formed during the reaction. The reactants produced 45.14 grams of a copper lysine amino acid chelate having a ligand to metal molar ratio of about 1:1.

Example 5

Preparation of Zinc Cysteine/Glycine Amino Acid Chelate

A solution comprising 56.08 grams of calcium oxide, 60.58 grams of cysteine, 37.53 grams of glycine, and 700 grams of water was prepared and allowed to react for 30 minutes while being stirred. Next, 161.44 grams of zinc sulfate was added and stirred until the zinc sulfate dissolved. In addition to the formation of the terra alba, 179.49 grams of a zinc cysteine/glycine amino acid chelate having a ligand to metal molar ratio of about 1:1 was formed.

Example 6

Preparation of Chromium Glycine Amino Acid Chelate

In 750 grams of water, 84.12 grams of calcium oxide was reacted with 150.14 grams of glycine for 30 minutes to form a liquid reaction mixture. Next, 250.09 grams of chromium sulfate hexahydrate was added to the reaction mixture and stirred. About 219 grams of a chromium glycine amino acid chelate having a ligand to metal molar ratio of about 2:1 was produced in addition to the terra alba formed.

Example 7

Preparation of Copper Serine Amino Acid Chelate

A reaction mixture comprised of 74.1 grams of calcium hydroxide, 105.1 grams of serine, and 700 grams of water was prepared and allowed to react for 30 minutes while stirring. Next, 249.6 grams of copper sulfate pentahydrate was stirred into the solution and a white precipitate of calcium sulfate formed. Once the reaction was complete, a total of 184.7 grams of a copper serine amino acid chelate having a ligand to metal molar ratio of about 1:1 was produced.

Example 8

Preparation of Chromium Glycine Amino Acid Chelate

In 750 grams of water, 111.14 grams of calcium hydroxide was reacted with 150.14 grams of glycine for 30 minutes. Next, 250.09 grams of chromium sulfate was added and stirred until the calcium sulfate ceased significant precipitation. About 219 grams of a chromium amino acid chelate having a ligand to metal molar ratio of about 2:1 was produced.

Example 9

Preparation of Copper Glycine Amino Acid Chelate

To about 1500 grams of water was dissolved 150.14 grams of glycine, 114.51 grams of calcium oxide, and 508.2 grams of copper sulfate pentahydrate. The solution was constantly stirred while the copper sulfate and the calcium oxide was dissolved. As the copper sulfate went into solution, a white precipitate of calcium sulfate formed. About 277 grams of a copper glycine amino acid chelate having a ligand to metal molar ratio of about 1:1 was produced.

Example 10

Preparation of Copper Lysine Amino Acid Chelate

To about 700 grams of water was added about 49.94 grams of copper sulfate pentahydrate. The solution was stirred until the copper sulfate dissolved. Next, 32.66 grams of lysine was stirred into the solution for about 30 minutes. To the aqueous solution was added 5.58 grams of calcium oxide. Again the solution was continually stirred until all of the calcium oxide was dissolved. As the calcium oxide went into solution, a white precipitate of calcium sulfate formed. Additionally, there was recovered 45.14 grams of a copper lysine amino acid chelate having a ligand to metal molar ratio of about 1:1.

Example 11

Comparison Between Amino Acid Chelates and Amino Acid Chelates in the Presence of Terra Alba A 10:1 mixture of copper glycinate to terra alba (CaSO$_4$) [Sample 1] was prepared and shaken together in a plastic bag. Next, a pure copper glycinate without the presence of terra alba [Sample 2] was also prepared and shaken in a plastic bag. With regard to Sample 1, no particulates stuck to the walls of the bag. Conversely, with Sample 2, a blue haze of product stuck the walls of the bag. This demonstrated that Sample 1 was less electrostatic.

Sample 1 was further compared to Sample 2 by rubbing a portion of each between the thumb and finger. Sample 2 quickly balled up with moisture from the thumb and finger as well as from the surrounding air. Conversely, Sample 1 did not ball up. This demonstrated that Sample 1 was less hygroscopic.

The particle size found in Sample 1 and Sample 2 was about 70 mesh. Thus, the presence of terra alba did not significantly change the particle size.

Finally, Sample 2 was added to a stimulated gastric solution which caused the product to change color. Sample 1 was similarly added to a stimulated gastric solution. However, no color change was observed demonstrating the stabilizing effect of terra alba on an amino acid chelate in an acid environment.

While the invention has been described with reference to certain preferred embodiments, those skilled in the art will appreciate that various modifications, changes, omissions, and substitutions can be made without departing from the spirit of the invention. It is intended, therefore, that the invention be limited only by the scope of the following claims.

We claim:

1. A method of preparing amino acid chelates free of interfering ions comprising reacting in an aqueous solution,
    a) a calcium oxide or hydroxide,
    b) an amino acid, and
    c) a soluble metal sulfate salt at a ratio sufficient to allow substantially all of the reactants present in solution to react forming a positively charged metal amino acid chelate having a hydroxide counter-ion, and calcium sulfate, and wherein said metal amino acid chelate has a ligand to metal molar ratio from about 1:1 to 2:1.

2. A method as in claim 1 wherein the metal is divalent and the ligand to metal molar ratio is about 1:1.

3. A method as in claim 1 wherein the metal is trivalent and the ligand to metal molar ratio is about 2:1.

4. A method as in claim 1 wherein said amino acid is selected from the group consisting of alanine, arginine, asparagine, aspartic acid, cysteine, cystine, glutamine, glutamic acid, glycine, histidine, hydroxyproline, isoleucine, leucine, lysine, methionine, ornithine, phenylalanine, proline, serine, threonine, tryptophan, tyrosine, valine, and combinations thereof, and dipeptides, tripeptides, and tetrapeptides formed by any combination of said amino acids thereof.

5. A method as in claim 1 wherein said metal is a divalent or trivalent cation selected from the group consisting of Cu, Zn, Fe, Cr, Co, Mg, Mn, and combinations thereof.

6. A method as in claim 1 wherein said soluble metal sulfate salt is a member selected from the group consisting CUSO$_4$, ZnSO$_4$, FeSO$_4$, COSO$_4$, MnSO$_4$, MgSO$_4$, Fe$_2$(SO$_4$)$_3$, Cr$_2$(SO$_4$)$_3$, and combinations thereof.

7. A method as in claim 1 wherein said amino acid is glycine and said metal amino acid chelate is selected from the group consisting of copper glycinate, zinc glycinate, iron glycinate, iron bisglycinate, chromium bisglycinate, cobalt glycinate, magnesium glycinate, manganese glycinate, and combinations thereof.

8. A method as in claim 1 wherein said metal amino acid chelate has a ligand to metal molar ratio of about 1:1 and the reaction is further defined by:

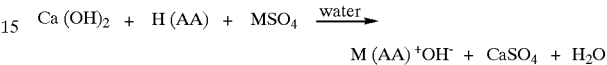

where H(AA) is one or more naturally occurring amino acids; H when disassociated from AA is a hydrogen ion donor from the carboxyl group present on the amino acid, and M is selected from the group consisting of Cu, Zn, Fe, Co, Mg, Mn, and combinations thereof.

9. A method as in claim 1 wherein said metal amino acid chelate has a ligand to metal molar ratio of about 1:1 and the reaction is further defined by:

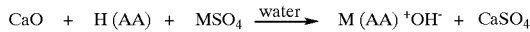

where H(AA) is one or more naturally occurring amino acids; H when disassociated from AA is a hydrogen ion donor from the carboxyl group present on the amino acid; and M is selected from the group consisting of Cu, Zn, Fe, Co, Mg, Mn, and combinations thereof.

10. A method as in claim 1 wherein said metal amino acid chelate has a ligand to metal molar ratio of about 2:1 and the reaction is further defined by:

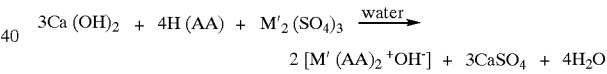

where H(AA) is one or more naturally occurring amino acids; H when disassociated from AA is a hydrogen ion donor from the carboxyl group present on the amino acid; and M' is selected from the group consisting of Fe, Cr, and combinations thereof.

11. A method as in claim 1 wherein said metal amino acid chelate has a ligand to metal molar ratio of about 2:1 and the reaction is further defined by:

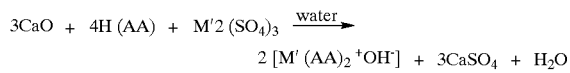

where H(AA) is one or more naturally occurring amino acids; H when disassociated from AA is a hydrogen ion donor from the carboxyl group present on the amino acid; and M' is selected from the group consisting of Fe, Cr, and combinations thereof.

12. A method as in claim 1 wherein said calcium sulfate is substantially separated out.

13. A method as in claim 1 wherein said calcium sulfate is not separated out.

14. A method as in claim 1 further comprising a subsequent step of drying the metal amino acid chelate.

15. An amino acid chelate free of interfering ions prepared by reacting in an aqueous solution
   a) a calcium oxide or hydroxide,
   b) an amino acid, and
   c) a soluble metal sulfate salt at a ratio sufficient to allow substantially all of the ions present in solution to react forming a charged metal amino acid chelate having a hydroxide counter-ion, and calcium sulfate, and wherein said metal amino acid chelate has a ligand to metal molar ratio from 1:1 to 2:1.

16. An amino acid chelate as in claim 15 wherein the metal is divalent and the ligand to metal molar ratio is about 1:1.

17. An amino acid chelate as in claim 15 wherein the metal is trivalent and the ligand to metal molar ratio is about 2:1.

18. An amino acid chelate as in claim 15 wherein said amino acid is selected from the group consisting of alanine, arginine, asparagine, aspartic acid, cysteine, cystine, glutamine, glutamic acid, glycine, histidine, hydroxyproline, isoleucine, leucine, lysine, methionine, ornithine, phenylalanine, proline, serine, threonine, tryptophan, tyrosine, valine, and combinations thereof, and dipeptides, tripeptides, and tetrapeptides formed by any combination of said amino acids thereof.

19. An amino acid chelate as in claim 15 wherein said metal is a divalent or trivalent cation selected from the group consisting of Cu, Zn, Fe, Cr, Co, Mg, Mn, and combinations thereof.

20. An amino acid chelate as in claim 15 wherein said soluble metal sulfate salt is a member selected from the group consisting $CuSO_4$, $ZnSO_4$, $FeSO_4$, $CoSO_4$, $MnSO_4$, $MgSO_4$, $Fe_2(SO_4)_3$, $Cr_2(SO_4)_3$, and combinations thereof.

21. An amino acid chelate as in claim 15 wherein said amino acid is glycine and said metal amino acid chelate is selected from the group consisting of copper glycinate, zinc glycinate, iron glycinate, iron bisglycinate, chromium bisglycinate, cobalt glycinate, magnesium glycinate, manganese glycinate, and combinations thereof.

22. An amino acid chelate having the formula:

$$M(AA)^+OH^-$$

where AA is an anion of one or more naturally occurring amino acids, and M is a divalent metal ion.

23. An amino acid chelate as in claim 22 wherein M is selected from the group consisting of Cu, Zn, Fe, Co, Mg, Mn, and combinations thereof.

24. An amino acid chelate having the formula:

$$M'(AA)_2^+OH^-$$

where AA is an anion of one or more naturally occurring amino acids, and M' is a trivalent metal ion.

25. An amino acid chelate as in claim 24 wherein M' is selected from the group consisting of Fe, Cr, and combinations thereof.

* * * * *